Nov. 1, 1966 R. S. MOORE Plant Pat. 2,683
ROSE PLANT
Filed Sept. 24, 1965
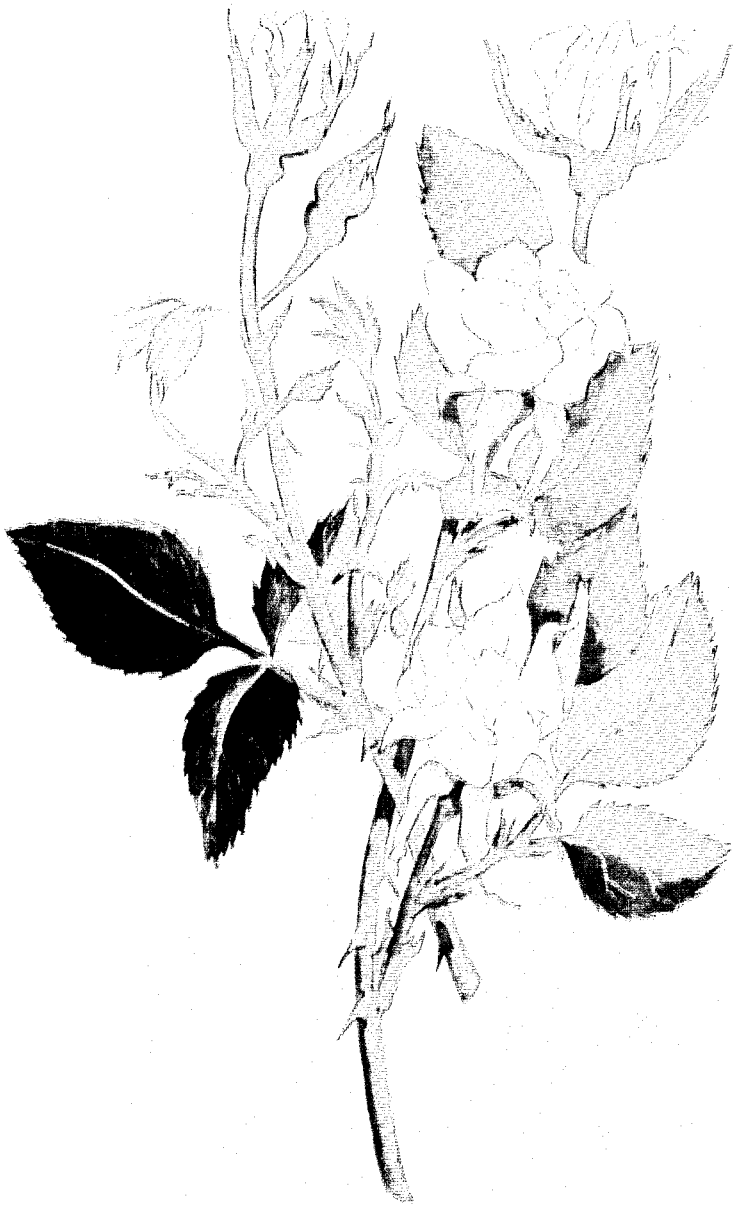
WITNESS
Jeanette Nunn Copley
INVENTOR
Ralph S. Moore United States Patent Office Plant Pat. 2,683
Patented Nov. 1, 1966

2,683
ROSE PLANT
Ralph S. Moore, 2519 E. Mineral King,
Visalia, Calif. 93277
Filed Sept. 24, 1965, Ser. No. 490,150
1 Claim. (Cl. Plt.—8)

The present invention relates to a new and distinct variety of hardy, dwarf, bush type plant of the miniature class; the variety being primarily characterized—as to novelty—by pointed, hybrid tea shaped white buds, the outer petals of which at times are pale green-white and which open into very double, long lasting, white flowers.

The variety is further characterized by:

An abundance of bloom, with flowers borne singly or several to stem in loose clusters.

Little or no fragrance.

Buds which keep exceptionally long as cut flowers.

A plant which is vigorous, of rounded upright shape, and with semi-glossy, small foilage with pointed leaflets; the pointed buds being similar to Pink Cameo (United States Plant Patent No. 1,451) and the very double flowers resembling Lolipop (United States Plant Patent No. 2,080) except that the present variety is white. The plant which has a normal average height of 12" to 14" at maturity can be easily maintained at 10" or less by occasional trimming.

A plant which grows and blooms satisfactorily both in the greenhouse and outdoors; is a good plant for growing in pots; and provides excellent garden decoration as well as cut flowers.

The present variety of miniature rose was originated by me at my nursery located at Visalia, California, under conditions of careful control and observation, as a cross between Little Darling (a floribunda rose, United States Plant Patent No. 1,581) as the seed parent, and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foilage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers:

*Continuity.*—Continuous.

*Fragrance.*—Little or none.

Flowers borne: Singly and several together (3 to 5) on stiff, medium length stems.

Quantity of bloom: Abundant both outside and in greenhouse.

Bud:

*Peduncle.*—Medium length; slender, stiff; erect; normal green; few very small short hairs. Before calyx breaks, size—small. Form long; pointed; with several foliaceous appendages and a few very tiny short hairs on surface of bud; with foliaceous parts extending beyond the tip of the bud equal to one half or more of its length.

*Color.*—Medium green. As calyx breaks, color—almost Pea Green 61/3. As first petal opens—almost Pea Green 61/3; size small.

*Form.*—Long; pointed, becoming slightly cupped as it opens.

*Opening.*—Seems to open well in all weather.

Bloom:

*Size when fully open.*—Small, averaging 1¼" to 1½".

*Petalage.*—Very double—50 petals arranged regularly.

*Form.*—Slightly cupped at first with petals rolled loosely outward (and somewhat wavy), and at maturity being loosely rolled outward and wavy giving the flower a caranation-like appearance.

Petals: Fairly thick with good substance; satiny both inside and outside. Shape: Outside—oval (broad lanceolate); intermediate—lanceolate; inside—lanceolate.

Color: Newly opened flower from plant grown outdoors (September 1965) Visalia, California,

*Outside petal.*—Outside surface—white (almost Pea Green 61/3); inside surface—white (almost Pea Green 61/3).

*Intermediate petal.*—Outside surface—white shading to pale greenish-yellow at base; inside surface—same as outside.

*Inner petal.*—Outside surface—white shading to pale greenish-yellow at base; inside surface—white shading to yellow at base.

*General color effect newly opened flower.*—White. Three days open—white.

*Behavior.*—Petals persist for time then drop off. In cooler fall weather (outside) older petals may show tips or other areas which become pink giving the flower a somewhat variegated (but not unpleasing) appearance.

*Flower longevity (September 1965).*—Bush in garden or pot—5 to 7 days or longer. Cut flowers at living room temperature—4 to 7 days.

Reproductive organs:

*Stamens.*—Few; arranged irregularly about pistil; often mixed with petaloids.

*Filaments.*—Short; yellow.

*Pollen.*—Scarce.

*Pistils.*—Average.

*Styles.*—Uneven; medium length; bunched.

*Stigma.*—Pale, nearly white.

*Ovaries.*—All enclosed in calyx.

*Hips.*—None.

*Sepals.*—Permanent; spear shaped; recurved.

*Seeds.*—None.

Foliage:

*Leaves.*—Compound of five leaflets; abundant; small to moderately small; leathery; semi-glossy.

*Leaflets.*—Shape—apex acute; base acute to rounded acute. Margin serrate. Color—bright normal green; new growth sometimes tinted bronze. Rachis—strong; upper side smooth, grooved; under side sparsely thorny. Stipules—medium length; medium width; medium length points, turning out at an angle of about 45 degrees.

Growth:

*Habit.*—Dwarf; bushy; upright; much branched.

*Growth.*—Free; vigorous.

*Canes.*—Medium; slender.

*Main canes.*—Color—dull green. Thorns—moderately thorny; medium length; hooked slightly downward; slender; sharp point; color—medium brown. Prickles—none. Hairs—none.

*Branches.*—Color—medium green. Thorns—moderately thorny; medium length; straight but angled slightly downward; slender; sharp points; medium length oval base. Prickles.—none. Hairs—none.

*New shoots.*—Color—medium green, often tinted bronze. Thorns—moderately thorny; medium length; straight; angled slightly downward; base oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, dwarf, upright, much branched, bush type, as illustrated and described, characterized by buds and flowers resembling the Little Scotch (Plant Patent No. 1,952)

miniature rose in general form but white rather than straw yellow, and mature flowers more flat and of much greater substance and lasting quality, both on the plant and as cut flowers; and further characterized by long lasting buds of hybrid tea quality, a plant which is of vigorous and compact growth, easy to propagate from cuttings, abundant, disease resistant foliage, a profusion of bloom, with flowers borne singly or several to stem in loose clusters.

No references cited.

ABRAHAM G. STONE, *Primary Examiner.*

R. E. BAGWILL, *Assistant Examiner.*